United States Patent [19]

Courteille et al.

[11] Patent Number: 5,206,025
[45] Date of Patent: Apr. 27, 1993

[54] POROUS PHARMACEUTICAL FORM AND ITS PREPARATION

[75] Inventors: Frédéric Courteille, Cachan; Magali Vanhoeve, Savigny s/Orge, both of France

[73] Assignee: Rhone-Poulenc Sante, France

[21] Appl. No.: 892,673

[22] Filed: Jun. 4, 1992

Related U.S. Application Data

[63] Continuation of Ser. No. 526,726, May 22, 1990, abandoned.

[30] Foreign Application Priority Data

May 24, 1989 [FR] France .................. 89 06781

[51] Int. Cl.$^5$ ............................................ A61K 47/40
[52] U.S. Cl. ........................ 424/439; 424/438; 424/440; 424/441; 424/442; 424/464; 424/488; 514/58; 514/777; 514/937; 514/974; 536/103
[58] Field of Search ............... 424/438, 439, 464, 488, 424/440, 441

[56] References Cited

U.S. PATENT DOCUMENTS

| | | | |
|---|---|---|---|
| 3,778,510 | 12/1973 | Blonde | 514/779 |
| 4,371,516 | 2/1983 | Gregory et al. | 424/422 |
| 4,727,064 | 2/1988 | Pitha | 514/58 |
| 4,758,598 | 7/1988 | Gregory | 424/484 |
| 4,803,077 | 2/1989 | Mitsuhashi et al. | 424/439 |
| 4,849,425 | 7/1989 | Kondo et al. | 514/58 |
| 4,877,774 | 10/1989 | Pitha et al. | 514/58 |
| 4,883,785 | 11/1989 | Chow et al. | 536/46 |
| 5,079,237 | 1/1992 | Husu et al. | 424/488 |

OTHER PUBLICATIONS

Organic Chemistry, 5th Ed. R. T. Morrison, R. N. Boyd, 1987, p. 1337.

Primary Examiner—Thurman K. Page
Assistant Examiner—James M. Spear
Attorney, Agent, or Firm—Morgan & Finnegan

[57] ABSTRACT

New porous, unitary freeze-dried pharmaceutical form, of homogeneous appearance, consisting of:
a) an inclusion compound comprising:
 one or optionally more active substances,
 a predetermined quantity of cyclodextrin,
 optionally an additive facilitating inclusion,
b) at least one substance chosen from:
 diluents,
 binders; and
c) optionally one or more additives.

27 Claims, No Drawings

POROUS PHARMACEUTICAL FORM AND ITS PREPARATION

This is a continuation of co-pending application Ser. No. 07/526,726, filed on May 22, 1990, now abandoned.

FIELD OF THE INVENTION

The present invention relates to a new porous, unitary, freeze-dried, solid pharmaceutical form, of homogeneous appearance, and to the process for its preparation.

BACKGROUND OF THE INVENTION

French Patents 2,036,890 and 2,366,835 describe pharmaceutical forms which have the characteristic of dissolving or disintegrating rapidly in an aqueous medium or in saliva.

However, the problem of masking the taste of medications intended for oral administration without, however, affecting the bioavailability of the active substance has never been solved. Especially insofar as it applies to the administration of such pharmaceutical substances to a young child or to an elderly person and to any individual for whom swallowing is difficult and can present a problem.

As a result of its disintegtration or of its rapid dissolution in an aqueous medium or in saliva, the new pharmaceutical form according to the invention makes administration to such individuals possible, while combining the advantage of masking the taste of bitter, irritant, acidic, etc. substances or those of unacceptable taste, which used to not be easy to administer orally, together with the advantage of a controlled dissolution of the active substance ensuring the maintenance and even the improvement of the bioavailability of the product.

In addition, the new pharmaceutical form which offers the advantage of use by walking patients, also offers the advantage of being made available instantly in contrast to tablets or to gelatin capsules whose content is too compact to ensure a suitable rate of disintegration.

DESCRIPTION OF THE INVENTION

The new freeze-dried pharmaceutical form according to the invention consists of:
a) an inclusion compound comprising:
 one or optionally more active substances,
 a predetermined quantity of cyclodextrin,
 optionally an additive facilitating inclusion;
b) at least one substance chosen from:
 diluents,
 binders; and
c) optionally one or more additives intended to:
 improve the taste,
 improve the breaking up,
 modify the colour,
 improve the conservation.

An active substance suitable for this new pharmaceutical form means any biologically active matter and more particularly any molecule capable of presenting difficulties in formulation which are bound up with problems of taste, of low solubility or of insolubility, of instability and/or of bioavailability.

Without any limitation being implied, among the active subtances which are commonly employed there may be mentioned nonsteroid antirheumatics and antiinflammatories (ketoprofen, ibuprofen, flurbiprofen, indomethacin, phenylbutazone, allopurinol, etc.), opiate or other analgesics (paracetamol, phenacetin, etc.) cough suppressors (codeine, codethyline, alimemazine, etc.), psychotropics (trimipramine, amineptine, chlorpromazine and derivatives of phenothiazines, diazepam, lorazepan, nitrazepam, meprobamate, zopiclone, suriclone and derivaties of the cyclopyrrolone group, etc.), steroids (hydrocortisone, cortisone, progesterone, testosterone, prednisolone, triamcinolone, dexamethasone, betamethasone, paramethasone, fluocinolone, beclomethasone, etc.), barbiturate (barbital, allobartital, phenobarbital, pentobarbital, amobarbital, etc.), antimicrobials (perfloxacine and derivatives of the quinolone class, tetracyclines, synergistines, metronidazole, etc.), medications intended for the treatment of allergies, antiasthmatics, vitamins (vitamin A, vitamin E, D-group vitamins, vitamin K), antispasmodics and antisecretories (omeprazole), cardiovasculars and cerebral vasodilators (quinacainol, oxprenolol, propanolol, nicergoline, etc.), cerebral protectors, hepatic protectors, therapeutic agents of the gastrointestinal tract, contraceptives, vaccines, etc.

In addition, the new pharmaceutical form can permit a solid presentation of active substances which are liquid under normal conditions of use.

It is to be understood that this new unitary form can be applied to the administration of all sorts of substances, both in human and veterinary medicine and to nutritional agents, to diagnostic agents, to cosmetic, hygiene and dietetic agents (for example breath modification) or even in the context of food adjuvants.

The cyclodextrin employed may be chosen equally well from $\alpha$, $\beta$ or $\gamma$ cyclodextrins or cyclodextrins which are polymerized or substituted, for example, by hydroxyethyl or hydroxypropyl radicals, or aminocyclodextrins but, as a general rule, the use of $\beta$-cyclodextrin will be preferred.

A diluent is intended to mean pharmaceutically acceptable, preferably soluble materials which improve the physical properties of the new galenic form. These substances may be chosen especially from mannitol, lactose, glycine, sorbitol, glucose, maltodextrins, cyclodextrins or mixtures thereof, or optionally from oxides (magnesium oxide), carbonates (calcium carbonate), phosphates (tricalcium phosphate) or celluloses (microcrystalline cellulose).

A binder is understood to mean any water-soluble or dispersible material which is acceptable from the viewpoint of pharmaceutics and inert towards the inclusion compound. These materials are chosen especially from polypeptides such as gelatine or partially hydrolyzed gelatine, colloids, polysaccharides of high molecular weight, high polymers capable of yielding colloidal solutions, for example natural resins (gum arabic, gum tragacanth, etc.), synthetic or semisynthetic resins (glycosylglucans, xanthan gum, etc.), dextran, dextrin, alginates (sodium alginate), pectinates, cellulose derivatives (microcrystalline cellulose, carboxymethyl cellulose, etc.), water-dispersible starch derivatives, colloidal silicas, bentonites or, furthermore, other support materials such as polyvinyl alcohol, polyvinylpyrrolidone, polyethylene glycols (especially PEG 20,000 and PEG 6,000), acrylic polymers or copolymers, or, furthermore, mixtures of substances such as those mentioned above.

It is to be understood that the new pharmaceutical form must necessarily contain at least one substance chosen from the abovementioned diluents and binders, but it may also be advantageous to involve one or more diluents and/or one or more binders at the same time.

In addition, the new galenic form may contain other additives, such as colorants, taste-modifiers, preserving agents, agents intended to prevent breaking up, or any other substance compatible with the remainder of the mixture.

The taste-modifiers may be especially sucrose, glucose, xylose, sorbitol, mannitol, xylitol, saccharin, saccharinates, cyclamates, aspartame or citric, ascorbic or tartaric acids, or any other substance which is usually employed for modifying taste in the foodstuff or pharmaceutical industry and which is compatible with the products with which it is in contact.

The coloring agents and preserving agents are those usually employed in the pharmaceutical and food industry.

Among the agents which improve breaking up, use may be made of hydrophilic diluents or of disintegrating agents, especially sugars (for example lactose, glucose, mannitol, levulose, sorbitol and maltodextrin) or silica.

The agents which facilitate the inclusion may be chosen especially from buffer or other electrolyte solutions or from cosolvents for the active substance. For example, sodium chloride or sodium dioctylsulphosuccinate may be advantageously added.

The present invention also relates to the preparation of the new pharmaceutical form according to the following operations:

1) preparation of a dough containing the various constituents listed above at a) to c), together with a suitable quantity of water so as to adjust the viscosity of the suspension obtained, 2) division of the dough into unitary quantities of predetermined shape and volume, 3) freeze-drying.

It is to be understood that the inclusion compound formed by the active substance and cyclodextrin can be alternatively prepared before the constitution of the dough to be freeze-dried, or in situ during the preparation of the dough. This second alternative is particularly advantageous, since it makes it possible to prepare the mixture to be freeze-dried in a single operation.

Furthermore, it is to be understood that the division of the product may also be carried out mechanically after freeze-drying, but it is preferable to divide the dough into cells of predetermined form and dimensions, before the freeze-drying operation, the dosage of the active substance(s) and the shape and the dimensions of the cells being calculated so as to obtain a precise quantity of active substance in each unit dose.

When the inclusion compound is prepared beforehand, it may be obtained by a liquid route (coprecipitation) or by a solid route (blending). The relative quantity (in moles) of the active substance relative to cyclodextrin varies in proportions ranging from 1/1 to 1/10. The compound may be prepared especially by mixing suitable quantities in the presence of a small quantity of water (so as to obtain a fairly fluid dough to make the inclusion process possible) followed by drying of the suspension obtained.

When the inclusion compound is prepared in situ, the constituents are introduced directly into the dough intended for the freeze-drying, in proportions identical with the proportions defined above.

As a general rule, the total quantity of inclusion compound can vary as a function of the nature of the active substance, but it is obvious that this new solid form can make it possible to prepare unit doses with a high content of active substance. As a general rule, the quantity of inclusion compound may go up to 98% by weight relative to the solids content but it is preferred that the quantity of inclusion compound constitute from 18 to 98% of the dry mass of the mixture.

Another advantage of the new galenic form is to make it possible to produce a better homogeneity of mixing in the case of active substances whose dosages are very low, because of the increase in the overall molecular weight when the inclusion compound is produced.

The diluents may constitute from 0 to 80% relative to the total dry mass of the freeze-dried product it being understood that in such case, the preferred quantity constitute from 0.5 to 3% of the dry mass.

As a general rule, binders are not always indispensable, but they may constitute from 0.01 to 10% relative to the dry mass of the freeze-dried product.

The quantity of water introduced to form the dough to be freeze-dried is determined so that the suspension obtained has rheological characteristics permitting good division of the product (flow, homogeneity of mixing, uniformity of the divided volume, stability of the suspension during the divsion). In most cases the quantity of water will be adjusted so that the solid mass constitutes approximately 50% of the mixture. As a general rule, it may vary from 35 to 80% relative to the dry mass of the mixture.

The mixture constituting the dough to be freeze-dried or the inclusion compound (when the latter is prepared separately) are generally prepared at room temperature; but they can also be prepared at a temperature ranging from 5° C. up to approximately 80° C. (provided that the active substance in question is stable at this temperature).

Modifications to the quantity of binder, diluent or water, or to the nature of the constituents can, of course, entail modifications in the quality of the unitary form prepared and thus makes it possible to prepare a product with controlled dissolution.

The division of the suspension is carried out manually or automatically, in the primary packaging material. As a general rule, the cells provided for this purpose are made of polyvinyl chloride.

The freeze-drying imparts a porous structure to the new pharmaceutical form, permitting a fast breaking up in water or directly in saliva.

The new unitary solid form according to the invention is very particularly indicated for oral administration, but it can also be employed for administration by rectal or vaginal route.

Bearing in mind the advantages which it offers, the new unitary form is very particularly indicated for pharmaceutical formulations intended for paediatrics or for geriatrics. It is of particular interest in the case of active substances which are insoluble, unstable, unacceptable in taste or of insufficient bioavailability.

EXAMPLES

The following examples illustrate the present invention.

EXAMPLE 1

A premix containing the active substance and the excipients and which has the following composition (unitary formula) is prepared in a planetary mixer of Olsa type:

Ketoprofen: 0.025 g
β-Cyclodextrin: 0.554 g
Dextran 70: 0.020 g
Mannitol: 0.100 g
Flavoring: 0.030 g
Aspartame: 0.010 g The powder mass is mixed dry for 30 minutes and 0.310 g of water per unit is then added to it and it is blended for one hour at room temperature.

The concentrated suspension thus obtained is divided using a Citus divider into 1.2-cc polyvinyl chloride cells.

The polyvinyl chloride cell sheet containing the suspension is introduced into a freeze-drier immediately after division, to be frozen at a temperature of −50° C. at atmospheric pressure, for approximately 2 hours. After drying for 12 hours under reduced pressure, the temperature is progressively raised again to 30° C. in 5° C. steps.

The freeze-dried products obtained are packaged directly by heat-sealing with an aluminium foil which is sufficiently thin to allow them to be pushed out of the cells without crumbling.

The breaking up time of the freeze-dried product in water varies from 1 to 3 minutes.

EXAMPLE 2

The procedure described above in Example 1 but starting with the constituents below (unitary formula):

Ketoprofen: 0.050 g
β-Cyclodextrin: 1.108 g
Dextran 70: 0.020 g
Flavouring: 0.030 g
Aspartame: 0.010 g followed by the addition of 0.480 g of water, is used to prepare freeze-dried products distributed into 1.6-cc polyvinyl choride cells, which have hardness and breaking up qualities suitable for their use according to the present invention.

EXAMPLE 3

The procedure described above in Example 1, but starting with the following constituents (unitary formula):

Ketoprofen: 0.025 g
β-Cyclodextrin: 0.558 g
Powdered silica: 0.004 g
Mannitol: 0.101 g
Lactose: 0.101 g
Flavoring: 0.036 g
Aspartame: 0.008 g followed by the addition of 0.500 g of water, is used to prepare freeze-dried products distributed into 1.6-cc polyvinyl chloride cells, which have hardness and breaking up qualities which are suitable for their use according to the present invention.

EXAMPLE 4

By proceeding as described above in Example 1 but starting with:

Ketoprofen: 0.025 g
β-Cyclodextrin: 0.558 g
Mannitol: 0.294 g
Lactose: 0.146 g
Flavoring: 0.046 g
Aspartame: 0.011 g followed by the addition of 0.648 g of water, blending for 1 hour at room temperature, division into 1.6-cc polyvinyl chloride cells and then freeze-drying and packaging, a freeze-dried product of good hardness and breaking up quality is obtained.

EXAMPLE 5

By proceeding as described above in Example 1, but starting from (unitary formula):

Ketoprofen: 0.025 g
β-Cyclodextrin: 0.557 g
Sodium dioctylsulphosuccinate: 0.001 g
Lactose: 0.086 g
Sorbitol: 0.029 g
Flavoring: 0.032 g
Aspartame: 0.007 g followed by the addition of 0.470 g of water, blending for 1 hour at room temperature, division into 1.2-cc polyvinyl chloride cells, and then freeze-drying and packaging, a freeze-dried product of suitable hardness and breaking up quality is obtained.

EXAMPLE 6

A premix of (unitary formula):

Ketoprofen: 0.025 g
β-Cyclodextrin: 0.558 g is prepared in a planetary mixer of Olsa type by stirring for 5 minutes.

The mixture obtained is wetted with water (small quantity), is blended at 30° C. for 2 hours 30 minutes and is then dried in an oven and screened on a 0.5-mm grid.

The inclusion compound thus obtained is mixed dry for 30 minutes with the following excipients (unitary formula):

Mannitol: 0.294 g
Lactose: 0.146 g
Flavoring: 0.046 g
Aspartame: 0.011 g

After addition of 0.864 g of water and blending for one hour, the suspension is divided into 1.6-cc polyvinyl chloride cells and is then freeze-dried and packaged as described above in Example 1.

EXAMPLE 7

The procedure described in Example 1, but using 700 mg of water per unit to prepare the dough to be freeze-dried, is used to prepare freeze-dried products containing 25 mg of trimipramine base of the following composition:

Trimipramine methanesulphonate: 33.16 mg
Dextran 70: 20.00 mg
β-Cyclodextrin: 1000.00 mg The freeze-dried products obtained are soluble, tasteless and nonhygroscopic.

EXAMPLES 8 TO 13

The active substance and β-cyclodextrin are mixed dry for 15 minutes in order to obtain a homogeneous mixture.

The mixture obtained is wetted with a sufficient quantity of water to obtain, after the addition of the complementary excipients, a pasty suspension which can be divided by hand (suitable viscosity). The maximum quantity corresponding to the filling limit of the cells is fixed at 1.35 g in the case of 1.2-cc cells.

Blending is carried out at intermediate speed, at room temperature, for 3 hours (arbitrary time). The complementary excipients are added 30 minutes before the end of the blending. The pasty suspension is divided into 1.2-cc polyvinyl chloride cells, followed by freeze-drying while maintaining a freezing plateau at $-10°$ C. for 1 hour.

EXAMPLE 8

Unitary formula:
Zopiclone: 0.030 g
β-Cyclodextrin: 0.220 g
Lactose: 0.250 g
Mannitol: 0.250 g
Orange flavoring: 0.030 g
Aspartame: 0.010 g After the addition of 0.500 g of water, blending, division and freeze-drying, a freeze-dried product of suitable hardness and breaking up quality (shorter than or equal to 3 minutes) is obtained.

EXAMPLE 9

Unitary formula:
Phenobartital: 0.100 g
β-Cyclodextrin: 0.490 g
Lactose: 0.100 g
Mannitol: 0.100 g
Orange flavoring: 0.030 g
Aspartame: 0.010 g After the addition of 0.500 g of water, blending, division and freeze-drying, a freeze-dried product of suitable hardness and breaking up quality (shorter than or equal to 3 minutes) is obtained.

EXAMPLE 10

Unitary formula:
Vitamin A: 0.060 g
β-Cyclodextrin: 0.148 g
Lactose: 0.300 g
Mannitol: 0.300 g
Orange flavoring: 0.030 g
Aspartame: 0.010 g After the addition of 0.500 g of water, blending, division and freeze-drying, a freeze-dried product of suitable hardness and breaking up quality (shorter than or equal to 3 minutes) is obtained.

EXAMPLE 11

Unitary formula:
Lemon essence: 0.025 g
β-Cyclodextrin: 0.250 g
Lyoc ® grade lactose: 0.050 g
Mannitol: 0.050 g
Aspartame: 0.005 g After the addition of 0.600 g of water, blending, division and freeze-drying, a freeze-dried product of suitable hardness and breaking up quality (shorter than or equal to 3 minutes) is obtained.

EXAMPLE 12

Unitary formula:
Natural pristinamycin: 0.100 g
β-Cyclodextrin: 0.490 g
Lactose: 0.100 g
Mannitol: 0.100 g
Orange flavoring: 0.030 g
Aspartame: 0.010 g After the addition of 0.750 g of water, blending, division and freeze-drying, a freeze-dried product of suitable hardness and breaking up quality (shorter than or equal to 3 minutes) is obtained.

EXAMPLE 13

Unitary formula:
Vitamin D3: 0.005 9
β-Cyclodextrin: 0.148 g
Lyoc ® grade lactose: 0.300 g
Mannitol: 0.300 g
Flavoring: 0.030 g
Aspartame: 0.010 g After the addition of 0.300 g of water, blending, division and freeze-drying, a freeze-dried product of suitable hardness and breaking up quality (shorter than or equal to 3 minutes) is obtained.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims. The references are hereby incorporated by reference.

We claim:

1. A porous, unitary, freeze-dried pharmaceutical form of homogeneous appearance, which consists of:
   a) an inclusion compound comprising: at least one pharmaceutically active substance and cyclodextrin, and
   b) at least one substance chosen from: diluents, binders;
said pharmaceutical form being prepared by carrying out the following operations:
   1) preparation of a dough containing the constituents a) and b), together with water so as to adjust the viscosity of the dough obtained,
   2) division of the dough into unitary quantities having shape and volume, and
   3) freeze drying.

2. The porous, unitary, freeze-dried pharmaceutical form, of homogeneous appearance, according to claim 1, wherein the active substance is chosen from the class of psychotropics, analgesics, antiinflammatories or vitamins.

3. The porous, unitary, freeze-dried pharmaceutical form, of homogeneous appearance, according to claim 1, wherein the active substance is ketoprofen.

4. The porous, unitary, freeze-dried pharmaceutical form, of homogeneous appearance, according to claim 1, wherein the active substance is zopiclone.

5. The porous, unitary, freeze-dried pharmaceutical form, of homogeneous appearance, according to claim 1, wherein the active substance is trimipramine.

6. The porous, unitary, freeze-dried pharmaceutical form, of homogeneous appearance, according to claim 1, wherein the active substance is phenobarbital.

7. The porous, unitary, freeze-dried pharmaceutical form, of homogeneous appearance, according to claim 1, wherein the active substance is vitamin A.

8. A process for the preparation of the pharmaceutical form according to claim 1, wherein the following operations are carried out:
   1) preparation of a dough containing the constituents listed at a) to b), in claim 1, together with water so as to adjust the viscosity of the dough obtained,
   2) division of the dough into unitary quantities having shape and volume,
   3) freeze-drying.

9. The process according to claim 8, wherein the inclusion compound is prepared separately before the preparation of the mixture to be freeze-dried.

10. The process according to claim 8, wherein the inclusion compound is prepared in situ during the operation of preparing the dough to be freeze-dried.

11. Method of using the unitary form according to claim 1, for administering compositions intended for human of veterinary medicine to mammals.

12. Method of using the unitary form according to claim 1, for administering to mammals compositions intended for diagnostic agents, hygiene, dietetics, cosmetology or animal feed.

13. The method according to claim 11, wherein the mammal is a human.

14. The method according to claim 11, wherein the mammal is an animal.

15. The porous, unitary, freeze-dried pharmaceutical form, according to claim 1, further comprising c) at least one additive to improve taste, improve breaking up, modify color, or improve conservation and said pharmaceutical form being prepared by carrying out the following operations:
   1) preparation of a dough containing the constituents a), b) and c), together with water so as to adjust the viscosity of the dough obtained,
   2) division of the dough into unitary quantities having shape and volume, and
   3) freeze drying.

16. The porous, unitary, freeze-dried pharmaceutical form, of homogeneous appearance, according to claim 1, further comprising an additive facilitating inclusion chosen from a buffer solution, an electrolyte solution or a cosolvent for the active substance.

17. The porous, unitary, freeze-dried pharmaceutical form, according to claim 1, wherein freeze drying is carried out after division of the dough.

18. The porous, unitary, freeze-dried pharmaceutical form, according to claim 1, wherein freeze drying is carried out before division of the dough.

19. The porous, unitary, freeze-dried pharmaceutical form, according to claim 1, wherein the inclusion compound is prepared in situ during the operation of preparing the dough to be freeze-dried.

20. The porous, unitary, freeze-dried pharmaceutical form, according to claim 1, wherein the inclusion compound is prepared separately before the preparation of the mixture to be freeze-dried.

21. The porous, unitary, freeze-dried pharmaceutical form, according to claim 17, wherein the active substance is ketoprofen.

22. The porous, unitary, freeze-dried pharmaceutical form, according to claim 19, wherein the active substance is ketoprofen.

23. The porous, unitary, freeze-dried pharmaceutical form, according to claim 20, wherein the active substance is ketoprofen.

24. A process for the preparation of the pharmaceutical form according to claim 15, wherein the following operations are carried out:
   1) preparation of a dough containing the constituents listed at a) to c), in claim 15, together with water so as to adjust the viscosity of the dough obtained,
   2) division of the dough into unitary quantities having shape and volume, and
   3) freeze drying.

25. The process according to claim 24, wherein freeze drying is carried out prior to division of the dough.

26. The process according to claim 24, wherein freeze drying is carried out after division of the dough.

27. A process for the preparation of the pharmaceutical form according to claim 16, wherein the following operations are carried out:
   1) preparation of a dough containing constituents a) and b) and the additive facilitating inclusion, in claim 16, together with water so as to adjust the viscosity of the dough obtained,
   2) division of the dough into unitary quantities having shape and volume, and
   3) freeze drying.

* * * * *